United States Patent
Evers (10) Patent No.: US 9,588,112 B2
(45) Date of Patent: Mar. 7, 2017

(54) DETECTION OF TARGET COMPONENTS WITH THE HELP OF INDICATOR PARTICLES

(75) Inventor: Toon Hendrik Evers, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1367 days.

(21) Appl. No.: 12/863,219

(22) PCT Filed: Jan. 19, 2009

(86) PCT No.: PCT/IB2009/050170
§ 371 (c)(1),
(2), (4) Date: Jul. 16, 2010

(87) PCT Pub. No.: WO2009/093160
PCT Pub. Date: Jul. 30, 2009

(65) Prior Publication Data
US 2010/0330698 A1    Dec. 30, 2010

(30) Foreign Application Priority Data

Jan. 22, 2008 (EP) .................................... 08100716

(51) Int. Cl.
*G01N 33/543* (2006.01)
*B82Y 25/00* (2011.01)
(Continued)

(52) U.S. Cl.
CPC ........ *G01N 33/54373* (2013.01); *B82Y 25/00* (2013.01); *B82Y 30/00* (2013.01);
(Continued)

(58) Field of Classification Search
CPC ...... B82Y 25/00; B82Y 30/00; G01N 27/745; G01N 33/542; G01N 33/54326; G01N 33/54373; G01N 21/552
(Continued)

(56) References Cited

U.S. PATENT DOCUMENTS

| 6,736,978 | B1* | 5/2004 | Porter et al. .................. 210/695 |
| 2005/0018725 | A1* | 1/2005 | Nurmikko ....................... 372/37 |

(Continued)

FOREIGN PATENT DOCUMENTS

| WO | 2005010542 A2 | 2/2005 |
| WO | 2005010543 A1 | 2/2005 |

OTHER PUBLICATIONS

Schotter et al: "Comparison of a Prototype Mangetoresistive Biosensor to Standard Fluorescent DNA Detection"; Biosensors and Bioelectronics, vol. 19, No. 10, May 2004, pp. 1149-1156.

(Continued)

*Primary Examiner* — Mark Shibuya
*Assistant Examiner* — Pensee Do (57) ABSTRACT

The invention relates to a system and a method for the detection of target components (102) in a sample with the help of indicator particles (101) distributed in said sample. The distance (d) between indicator particles (101) and a contact surface (112) is determined after the target components could bind to the contact surface and/or the indicator particles. Thus it is possible to detect how many target components (102) are bound without a need for a binding between indicator particles (101) and contact surface (112). Optionally the indicator particles (101) can be affected by a modulated force, e.g. via an electromagnet (141). The determination of the distance (d) between indicator particles (101) and contact surface (112) may for example be achieved by frustrated total internal reflection, measurement of magnetic fields, or FRET.

19 Claims, 6 Drawing Sheets

(51) Int. Cl.
*B82Y 30/00* (2011.01)
*G01N 27/74* (2006.01)
*G01N 33/542* (2006.01)
*G01N 21/552* (2014.01)

(52) U.S. Cl.
CPC ......... *G01N 27/745* (2013.01); *G01N 33/542* (2013.01); *G01N 33/54326* (2013.01); *G01N 21/552* (2013.01)

(58) Field of Classification Search
USPC ................................................. 436/526, 518
See application file for complete search history.

(56) References Cited

U.S. PATENT DOCUMENTS

| | | | |
|---|---|---|---|
| 2005/0191643 A1* | 9/2005 | Haugland et al. | 435/6 |
| 2008/0160623 A1* | 7/2008 | Su | 436/94 |
| 2009/0005259 A1* | 1/2009 | Drmanac | B82Y 10/00 506/9 |
| 2010/0092996 A1* | 4/2010 | Verschuren | G01N 21/552 435/7.1 |
| 2010/0187450 A1* | 7/2010 | Kahlman | G01N 21/552 250/573 |

OTHER PUBLICATIONS

Kotitz et al: "Squid Based Remanence Mearurements for Immunoassays"; IEEE Transactions on Applied Superconductivity, vol. 7, No. 2, Jun. 1997, pp. 3678-3681.

Graham et al: "Magnetoresistive-Based Biosnesors and Biochips"; Trends in Biotechnology, vol. 22, No. 9, Sep. 2004, pp. 455-462.

Bishop et al: "Competitive Displacement: A Sensitive and Selective Method for the Detection of Unlabeled Molecules"; Optics Express,, Vo. 15, No. 8, Apr. 2007, pp. 4390-4397.

Sapsford et al: "Demonstration of Four Immunoassay Formats Using the Array Biosensor"; Analytical Chemistry, vol. 74, No. 5, Mar. 2002, pp. 1061-1068.

Frutos et al: "Method for Detection of Single-Base Mismatches Using Bimolecular Beacons": Journal of the American Chemical Society, vol. 124, No. 11, 2002, pp. 2396-2397.

Sun et al: "Design and Performances of Immunoassay Based on SPR Biosensor with Magnetic Microbeads"; Biosensors and Bioelectronics, vol. 23, No. 4, 2007, pp. 473-478.

Blickle et al: "Evanescent Light Scattering with Magnetic Colloids"; Appled Phsics Letters, vol. 87, No. 101102, Januarty 2005, pp. 101102-1-101102-3.

* cited by examiner

DETECTION OF TARGET COMPONENTS WITH THE HELP OF INDICATOR PARTICLES

The invention relates to a method and a sensor system for the detection of target components in a sample that is provided in a sample chamber. Moreover, it relates to a computer program for executing such a method.

A magnetic sensor device is known from the WO 2005/010543 A1 and WO 2005/010542 A2 which may for example be used in a microfluidic biosensor for the detection of molecules, e.g. biological molecules, labeled with magnetic beads. The magnetic sensor device is provided with an array of sensor units comprising wires for the generation of a magnetic field and Giant Magneto Resistances (GMR) for the detection of stray fields generated by magnetized beads. The signal of the GMRs is then indicative of the number of the beads that are bound to an adjacent contact surface.

Based on this background it was an object of the present invention to provide alternative means for the detection of parameters that are related to target components in a sample, wherein it is desirable that these means can readily be adapted to different target components of interest.

This object is achieved by a method according to claim 1, a sensor system according to claim 2, and a computer program according to claim 11. Preferred embodiments are disclosed in the dependent claims.

The method according to the present invention serves for the detection of a parameter of interest that is related to target components in a sample, e.g. the amount/concentration of these target components, wherein the sample is typically provided in a sample chamber and wherein the target components may for example be biological substances like biomolecules, complexes, cell fractions or cells. The method comprises the following steps:

a) Distributing a quantity of indicator particles in the sample. The term "indicator particle" shall denote a particle that has some property (e.g. optical density, magnetic susceptibility, electrical charge, fluorescence, radioactivity, etc.) which can be detected. As the indicator particles will typically be atoms, molecules, complexes, nanoparticles, or microparticles, the quantity will usually comprise huge numbers of such indicator particles. In the following, reference to the indicator particles will therefore simply be made in the plural without the intention to exclude the theoretical case that the quantity may comprise just one single indicator particle.

Moreover, the distribution of the indicator particles in the sample may be done actively, for example by stirring a sample liquid to which indicator particles have been added, or passively, for example by diffusion or convection.

b) Letting target components bind to the indicator particles and/or to a contact surface, which may for example be a wall of a sample chamber comprising the sample. In this context, the term "letting" shall mean that conditions are provided under which target components—if they are present in the sample—can establish bindings to the indicator particles and/or the contact surface. Such conditions may comprise for example enough time, appropriate temperature, active external assistance by stirring the sample, etc.

The contact surface and/or the indicator particles may optionally be covered with binding sites that are specific for the target components of interest.

Moreover, it should be noted that the target components may be conformational variants of some basic molecule or complex.

c) Determining directly or implicitly the distance between indicator particles and contact surface in a region adjacent to the contact surface and estimating the parameter of interest from said distance. The region in which the distance is determined may optionally comprise the whole sample; typically it will however be restricted to a more or less small volume adjacent to the contact surface. The determination of the distance and the estimation of the parameter of interest are usually achieved with a sensor element and an associated evaluation module for evaluating the sensor signals.

Moreover, it should be noted that "the distance" between indicator particles and contact surface is actually a short notation for a parameter that is related to the distribution of all distances between indicator particles (in the considered region) and the contact surface. As the indicator particles are usually in continuous (Brownian) motion through the sample, said distribution is a distribution of distances over particles and time. The considered parameter of this complex distribution will typically first of all comprise an average over time, at least with respect to a short period of time during which external conditions (e.g. forces on the indicator particles) are constant and during which microscopic effects like Brownian motion average out. In this case a distribution of distances over particles remains. To reduce complexity further, a single characteristic value of this residual distribution may be considered, for example the mean distance of all considered indicator particles. As will be discussed below, another important example of such a characteristic value is the amount of indicator particles that reaches a minimal distance from the contact surface.

The determination step may optionally be executed separately for single indicator particles, thus providing information that is independent of the concentration of all indicator particles in the sample.

The described method has the advantage to provide information about target components in a sample without a need for a binding between indicator particles and said target components (this statement holds if a binding between target components and contact surface takes place, which will be assumed in the following; if however a binding between target components and indicator particles takes place, the following arguments hold mutatis mutandis for the contact surface instead of the indicator particles). This eases the design and choice of the indicator particles considerably and allows for example "label-free" assays which use the same type of indicator particle for a plurality of different target components to be determined. The method is based on the observation that the binding of target components to a contact surface (or to an indicator particle) will affect the distance between indicator particles in the sample and the contact surface, particular the minimal distance they can assume. Determining this distance therefore in turn allows conclusions on the binding between target components and contact surface (or indicator particles).

While the target components will in most cases bind either to the indicator particles OR to the contact surface, it is also comprised by the present invention that they bind to both the indicator particles AND the contact surface. In this case the chance that target components are captured is increased. Moreover, the distance between indicator particles and contact surface can be doubled at high target concentrations.

The invention further relates to a sensor system for the detection of a parameter of interest that is related to target components in a sample, said system comprising the following components:

a) A sample chamber in which the sample can be provided, said sample chamber having a contact surface. The "sample chamber" is typically an empty cavity or a cavity filled with some substance (e.g. a fluid) that may absorb a sample substance; it may be an open cavity, a closed cavity, or a cavity connected to other cavities by fluid connection channels.

The "contact surface" is an interface between the sample chamber and another component, e.g. a transparent carrier or some (e.g. semiconductor) substrate, at which target components can collect.

b) A quantity of indicator particles that can be distributed in the sample and that do not directly or via target components bind to the aforementioned contact surface.

c) A sensor element for determining directly or implicitly the distance between indicator particles and contact surface in a region adjacent to the contact surface.

The sensor system provides the hardware for the execution of a method of the kind described above, wherein the determination of the parameter of interest is typically done by an evaluation module, e.g. a microcomputer, coupled to the sensor element. Reference is therefore made to the above description of said method for more information on the details and advantages of the sensor system.

In the following, further developments of the invention will be described that relate to both the method and the sensor system.

The parameter of interest that is related to the target components and that shall be detected may be any value which can be estimated from the measured distance between indicator particles and contact surface. Typical examples of such a parameter of interest comprise the following values:

The amount and/or concentration of target components in a given region, e.g. in the whole sample.

A chemical modification of the target components, e.g. the binding of small molecules/ions or a modification by a chemical reaction/enzyme.

A physical property of the sample that induces a change in the distance between the indicator particles and the contact surface, for example the temperature, pH, and/or the ionic strength of the sample (which may for example induce conformational changes of a target component).

Furthermore, the absolute or relative amount of indicator particles to which target components are bound and/or the absolute or relative size of the contact surface to which target components are bound may be estimated from the determined distance. These values will in turn comprise information about the amount/concentration of target components in the sample, which is typically the information one is interested in.

The indicator particles may be any entities that have features which can readily be detected and used for determining their distance from the contact surface. As the indicator particles need not necessarily bind to the target components, the choice of possible indicator particles is quite large. They may particularly comprise magnetic beads, i.e. permanently magnetic or magnetizable nano- or microparticles which can be manipulated by external magnets and can be detected by magnetic sensors. The indicator particles may further comprise fluorescent particles which emit fluorescent light when being excited by a suitable radiation. The indicator particles may particularly comprise donor chromophores or acceptor chromophores, which transfer/accept energy in the process of fluorescent resonance energy transfer (FRET). It should be noted that the indicator particles may comprise a mixture of the aforementioned examples and/or particles that exhibit simultaneously several features, e.g. magnetism and fluorescence.

The distance of a fluorescent indicator particle from the contact surface may affect the amount of fluorescence light that is collected by a light sensor and/or the amount of excitation light said indicator particle is exposed to. Moreover, the minimal possible distance between a donor chromophore on an indicator particle and an acceptor chromophore on the contact surface (or vice versa) will critically affect the amount of FRET. Thus there are many mechanisms by which the distance between such indicator particles and the contact surface can be detected.

In another embodiment of the invention, a force is exerted on the indicator particles during the determination of their distance from the contact surface, for example a magnetic force, an electrical force, a dielectrophoretic force, a hydrodynamic force etc. Magnetic forces may for instance be exerted by a magnetic field generator, e.g. an electromagnetic coil or an additional current wire in the sensor system. The force may optionally be modulated and e.g. attract the indicator particles with varying strength to the contact surface. This helps to reveal the minimal distance the indicator particles can assume from the contact surface.

There are many different methods available for determining the distance between indicator particles and contact surface. According to a preferred embodiment, a light beam, which will be called "input light beam" in the following and which will typically be generated by a light source like a laser or an LED, is emitted onto the contact surface, where it interacts with the indicator particles (if present). The input light beam may particularly be emitted towards the contact surface under conditions of (frustrated) total internal reflection ((F)TIR). In this case, an evanescent wave will penetrate into the sample chamber with an exponentially decaying intensity, i.e. over a small distance only. Thus it is possible to restrict the effect of the input light to a region immediately adjacent to the contact surface. Light of the evanescent wave may for example be used to stimulate fluorescence of fluorescent indicator particles, and/or the indicator particles may scatter/absorb said light, leading to a frustrated total internal reflection in which the reduced amount of reflected light provides information about the indicator particles. In the latter case, there will usually be a light detector for determining the amount of light in the output light beam generated by frustrated total internal reflection at the contact surface.

In another embodiment of the invention, the indicator particles are magnetized or magnetizable, and the distance between indicator particles and contact surface is determined by the effect of the magnetic indicator particles on a magnetic sensor element. The magnetic sensor element may particularly be integrated into the substrate which exhibits the contact surface. It may comprise any device that is suited for the detection of magnetic fields, for example a coil, Hall sensor, planar Hall sensor, flux gate sensor, SQUID (Superconducting Quantum Interference Device), magnetic resonance sensor, magneto-restrictive sensor, or magneto-resistive sensor of the kind described in the WO 2005/010543 A1 or WO 2005/010542 A2, especially a GMR (Giant Magneto Resistance), a TMR (Tunnel Magneto Resistance), or an AMR (Anisotropic Magneto Resistance).

It was already mentioned that the indicator particles may comprise a component of a FRET system. Similarly, the contact surface may at least partially be covered with acceptor chromophores or donor chromophores that can serve as partners for corresponding indicator particles in a FRET process.

According to a further development of the invention, the concentration of indicator particles in the sample or at least in the region adjacent to the contact surface is measured by a suitable concentration measurement unit. This is particularly useful in embodiments in which a value is measured that depends both on the distance between indicator particles and the contact surface and on the concentration of indicator particles. In these cases, the concentration of indicator particles must be known in advance (e.g. based on the preparation of the sample) or by the mentioned measurement to allow a correct estimate of the distance one is interested in.

Another embodiment of the invention is characterized by at least two measurements which depend in a different way on the concentration of the indicator particles and their distance from the contact surface. The measurements may for example have the same dependence on the concentration of the indicator particles but a different dependence on the distance between indicator particles and contact surface (or vice versa). By a proper combination of the measurements, it is possible to determine the distance irrespective of the prevailing concentration of indicator particles. The measurements may be done in parallel, e.g. by a sensor element that comprises two differently designed sensitive paths, or sequentially, e.g. by making with one sensor element two or more measurements under different operating conditions.

The sensor system will typically comprise a programmable evaluation module, e.g. it may include a microprocessor or an FPGA. Accordingly, the present invention further includes a computer program product which provides the functionality of any of the methods according to the present invention when executed on a computing device.

Further, the present invention includes a data carrier, for example a floppy disk, a hard disk, or a compact disc (CD-ROM), which stores the computer product in a machine readable form and which executes at least one of the methods of the invention when the program stored on the data carrier is executed on a computing device.

Nowadays, such software is often offered on the Internet or a company Intranet for download, hence the present invention also includes transmitting the computer product according to the present invention over a local or wide area network. The computing device may include a personal computer or a work station. The computing device may include one of a microprocessor and an FPGA.

These and other aspects of the invention will be apparent from and elucidated with reference to the embodiment(s) described hereinafter. These embodiments will be described by way of example with the help of the accompanying drawings in which.

Like reference numbers or numbers differing by integer multiples of 100 refer in the Figures to identical or similar components.

Though the present invention will in the following be described with respect to a particular setup (using magnetic indicator particles and frustrated total internal reflection as measurement principle), it is not limited to such an approach and can favorably be used in many different applications and setups.

Figure 1:
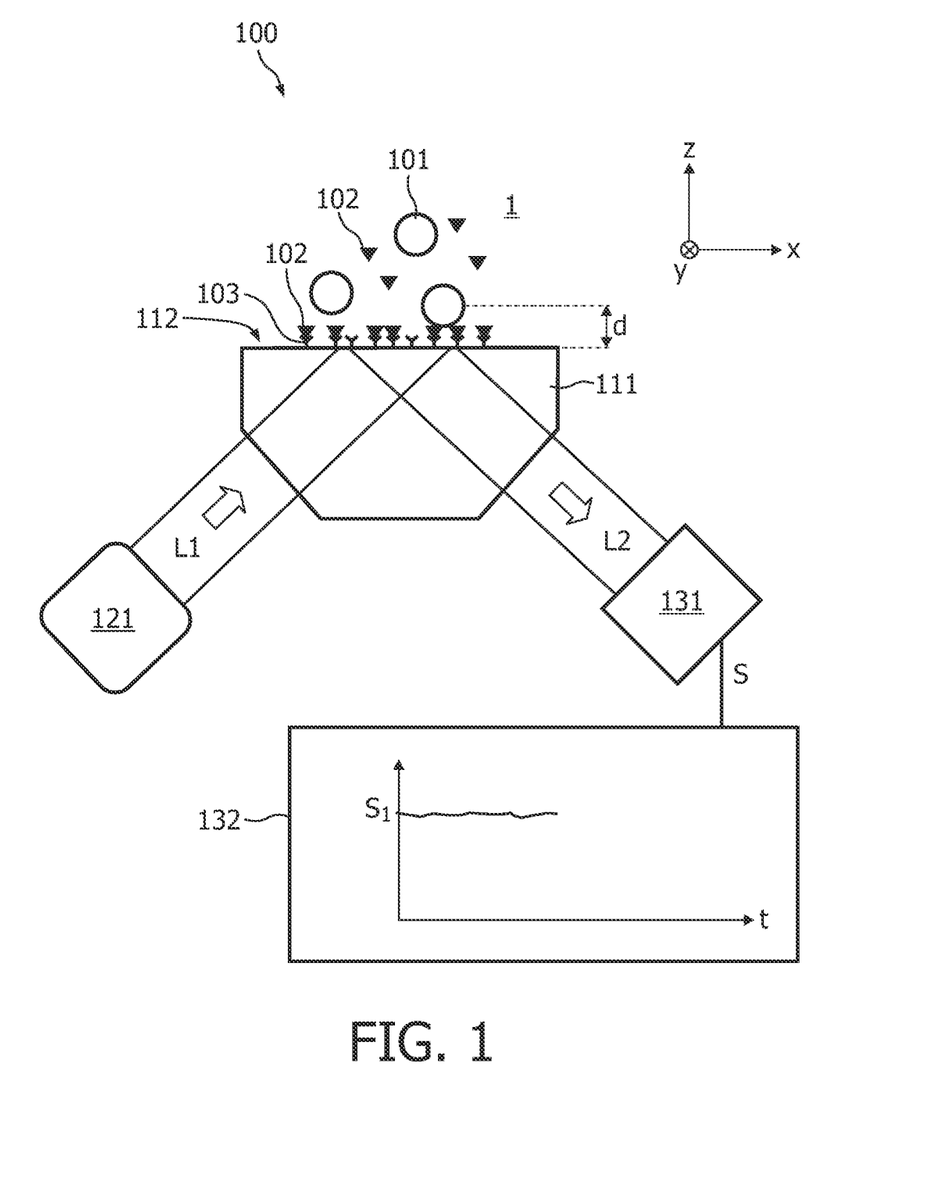
FIG. 1 shows schematically a sensor system according to the present invention when target components are bound to the contact surface.

FIG. 1 shows a general setup with a microelectronic sensor system 100 according to the present invention. A central component of this setup is the carrier 111 that may for example be made from glass or transparent plastic, e.g. as an injection-molded piece of a polymer like polystyrene. The carrier 111 is located next to a sample chamber 1 in which a sample fluid with target components 102 to be detected (e.g. drugs, antibodies, DNA, etc.) can be provided. The sample further comprises magnetic particles 101, for example superparamagnetic beads, which will be called "indicator particles" in the following. It should be noted that instead of magnetic particles other indicator particles, for example electrically charged or fluorescent particles, could be used as well.

The interface between the carrier 111 and the sample chamber 1 is formed by a surface called "contact surface" 112. This contact surface 112 is coated with capture elements 103, e.g. antibodies, which can specifically bind to target components 102.

The sensor system further comprises a light source 121 that generates an input light beam L1 which is transmitted into the carrier 111 through an "entrance window". As light source 121, e.g. a commercial CD ($\lambda$=780 nm), DVD ($\lambda$=658 nm), or BD ($\lambda$=405 nm) laser-diode can be used. A collimator lens may be used to make the input light beam L1 parallel, and a pinhole of e.g. 0.5 mm may be used to reduce the beam diameter. The input light beam L1 arrives at the contact surface 112 at an angle larger than the critical angle of total internal reflection (TIR) and is therefore totally internally reflected in an "output light beam" L2. The output light beam L2 leaves the carrier 111 through another surface ("exit window") and is detected by a light detector 131. The light detector 131 determines the amount of light of the output light beam L2 (e.g. expressed by the light intensity of this light beam in the whole spectrum or a certain part of the spectrum). The measured sensor signals are evaluated and optionally monitored over an observation period by an evaluation and recording module 132 that is coupled to the detector 131.

It is possible to use the detector 131 also for the sampling of fluorescence light emitted by fluorescent indicator particles which were stimulated by the input light beam L1, wherein this fluorescence may for example spectrally be discriminated from reflected light L2. Preferably, fluorescence will however be measured with a detector positioned out of the path of the output light beam L2 (not shown). Though the following description concentrates on the measurement of reflected light, the principles discussed here can mutatis mutandis be applied to the detection of fluorescence, too.

In many assays that use a setup of the kind described above, the indicator particle is used as a label, i.e. it is functionalized with a molecule (e.g. an antibody) that can bind to the target component. After the assay, the amount of indicator particles is detected and correlated to the amount of target components in the sample. For some assays or targets, it can however be difficult to label the target. A method will therefore be described in the following that allows a label-free detection of analytes. In label-free detection, there is no need to attach a label to the target, but the presence of the target is detected by other means. This enables a different type of biological assays.

The proposed method relies on the fact that, when a magnetic bead 101 is attracted to the contact surface 112, the distance d to which the bead 101 can approach the surface is determined by the height of the layer of target components 102 present at the surface 112. If a measurement signal S can be generated that is per bead 101 dependent on the distance d of the bead 101 from the surface 112, the presence or absence of target components 102 can be derived from the height of this signal S. In this manner, the target components 102 will generate a change in signal S without the indicator particles 101 being used as a real label that has to form a biological/chemical bond with the target molecule.

To achieve the aforementioned distance-dependent measurement, the described microelectronic sensor system applies the principle of frustrated total internal reflection (FTIR). This principle is based on the fact that an evanescent wave penetrates (exponentially dropping in intensity) into the sample 1 when the incident light beam L1 is totally internally reflected. If this evanescent wave then interacts with another medium like indicator particles 101 that are close enough to the contact surface 112, part of the input light will be coupled into the sample fluid (this is called "frustrated total internal reflection"), and the reflected intensity will be reduced (while the reflected intensity will be 100% for a clean interface and no interaction). Depending on the amount of disturbance, i.e. the amount of indicator particles 101 in the region adjacent to the contact surface 112 (i.e. within about 200 nm) and their distance d from said surface, the reflected intensity will drop accordingly. This intensity drop is a direct measure for the amount and distance d of indicator particles 101 in a small volume adjacent to the contact surface 112.

FIG. 1 illustrates this measurement principle for the case that target components 102 are bound to the binding sites 103 of the contact surface 112. The minimal (or average) distance d that indicator particles 101 can assume from the surface 112 is therefore comparatively large, leading to less scattering of evanescent waves and thus a higher measured intensity $S_1$ in the output light beam L2.

Figure 2:
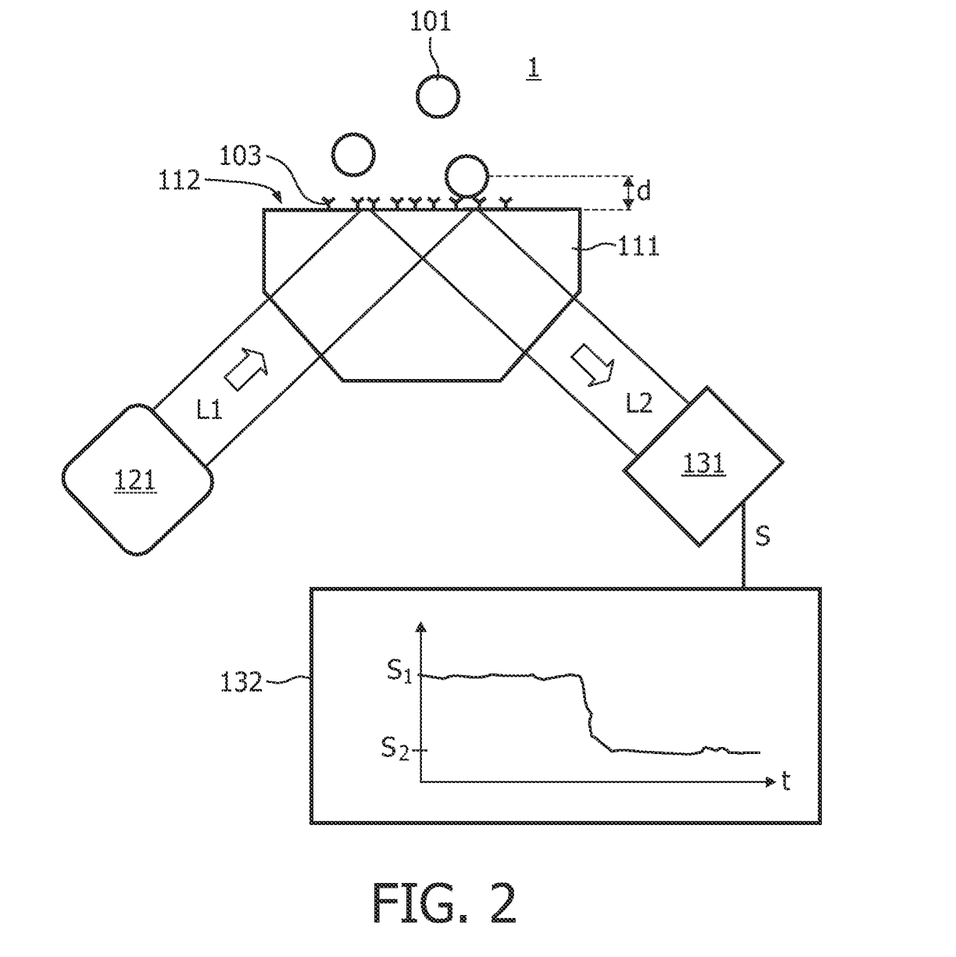
FIG. 2 shows the system of FIG. 1 when no target components are bound.

In FIG. 2, no target components 102 are bound. The indicator particles 101 can therefore get closer to the contact surface 112, leading to more scattering of evanescent waves and thus a corresponding drop in the measured intensity $S_2$ of the output light beam L2.

The FTIR detection has a typical depth resolution of roughly 5 nm. Because the intensity profile of the evanescent wave is dependent on (among other things) the angle of incidence and the wavelength of the light, the resolution can be adapted by varying these parameters. Larger wavelengths λ will for example increase the interaction distance of the evanescent waves, but the influence of the background liquid will still be very small. Another reason for a low background is that most biological materials have relatively low refractive indices near to the refractive index of water, i.e. n=1.3. The magnetic beads typically consist of a matrix material that has a significantly higher refractive index (n=1.6) causing the outcoupling of the signal. Furthermore, the magnetic beads contain potentially light scattering magnetic or magnetizable grains. Similar considerations hold for non-magnetic indicator particles which scatter and/or absorb light and therefore frustrate the total internal reflection.

The described procedure is independent of applied magnetic fields. This allows real-time optical monitoring of preparation, measurement and washing steps. The monitored signals can also be used to control the measurement or the individual process steps.

For the materials of a typical application, medium A of the carrier 111 can be glass and/or some transparent plastic with a typical refractive index of 1.52. Medium B in the sample chamber 1 will be water-based and have a refractive index close to 1.3. This corresponds to a critical angle of 60°. An angle of incidence of 70° is therefore a practical choice to allow fluid media with a somewhat larger refractive index.

The described optical read-out combined with magnetic indicator particles allows for large multiplexing possibilities for multi-analyte testing, as the contact surface 112 in a disposable cartridge can be optically scanned over a large area. Alternatively, large-area imaging is possible allowing a large detection array. Such an array (located on an optically transparent surface) can be made by e.g. ink jet printing of different binding molecules on the optical surface. The method also enables high-throughput testing in well-plates by using multiple beams and multiple detectors and multiple actuation magnets (either mechanically moved or electromagnetically actuated).

Figure 3:
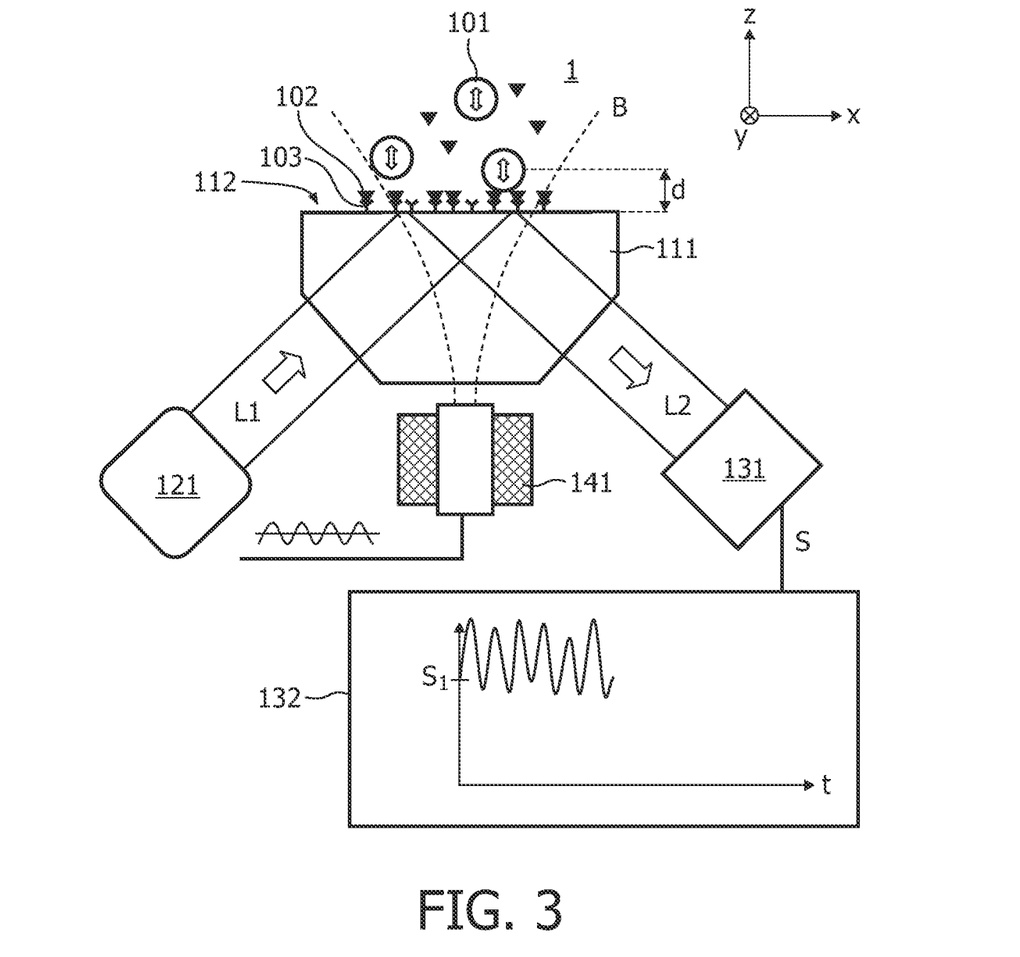
FIG. 3 shows the system of FIG. 1 with an additional magnet for exerting magnetic forces on the indicator particles.

In FIG. 3, a magnetic field generator 141 (e.g. an electromagnet with a coil and a core) has been added to the setup of the FIG. 1 for controllably generating a magnetic field B at the contact surface 112 and in the adjacent space of the sample chamber 1. With the help of this magnetic field, the indicator particles 101 can be manipulated, i.e. be magnetized and particularly be moved (if magnetic fields with gradients are used). Thus it is for example possible to attract indicator particles 101 to the contact surface 112. During pulsed actuation, indicator particles 101 are repeatedly pulled to the surface 112, leading to the time-varying signal change illustrated in the inset of the evaluation module 132. All the low points in this graph correspond to a moment when the beads 101 are closest to the surface 112. As target components 102 are bound to the binding sites 103 of the contact surface 112, these low points lie at a comparatively high value $S_1$.

Figure 4:
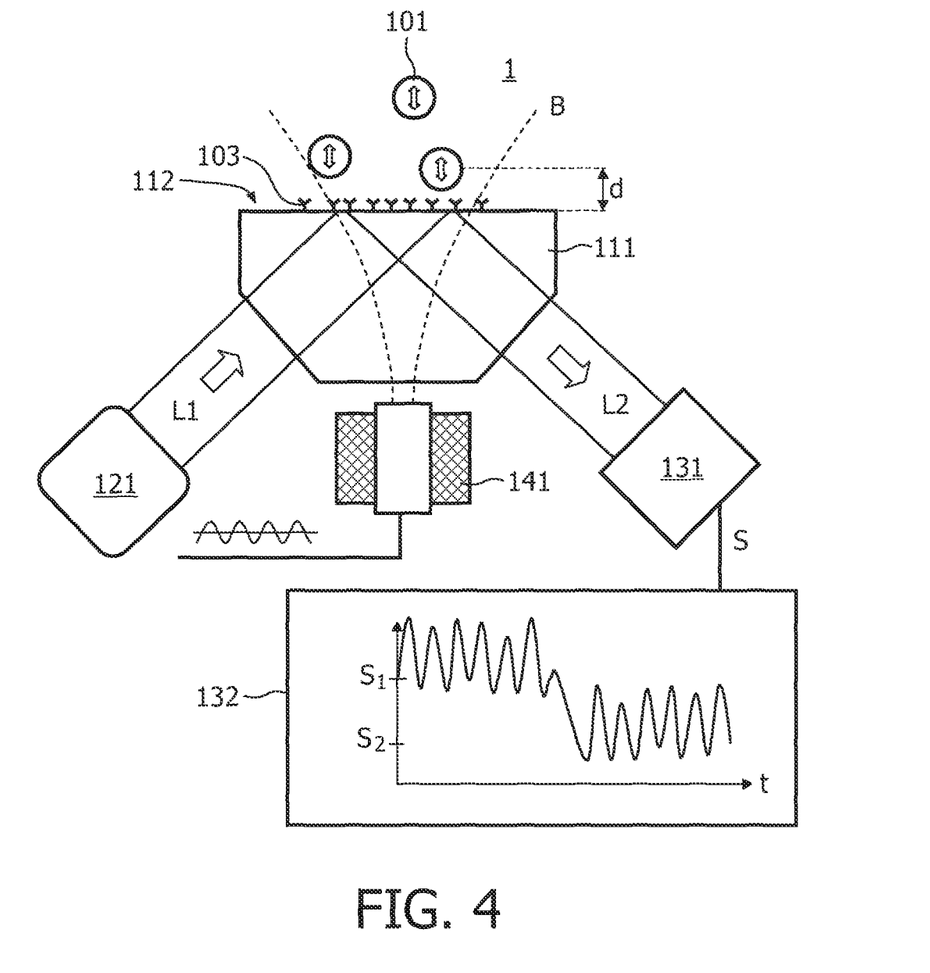
FIG. 4 shows the system of FIG. 3 when no target components are bound.

In FIG. 4, no target components 102 are bound. The indicator particles 101 can therefore get closer to the contact surface 112 during their pulsed attraction, leading to a lower measurement signal $S_2$. Experiments show that the average of the local minima in the signal S shows a clear difference for the situation when targets 102 have bound to the contact surface 112 or not.

In principle any detection technology that shows distance dependence from the contact surface can be used, for example a magnetic detection as disclosed in WO 2005/010543 A1. The FTIR detection described above is based on scattering/absorption of the indicator particles. However, in combination with fluorescent (magnetic) indicator particles, the evanescent wave could also be used to excite the fluorescent particles. Because the intensity of the evanescent wave decays exponentially with the distance from the surface, indicator particles that are closer to the surface will emit more light.

The height of the obtained signal using the FTIR or fluorescent detection technique described above is not only dependent on the distance of the indicator particles from the contact surface, but also on the number of indicator particles close to the surface. It is therefore necessary to carefully control the concentration of indicator particles used in an assay. The distance could also be measured independently from the bead concentration by using two evanescent waves with a different depth profile. For example, if two different wavelengths (and/or two different angles of incidence) are used, both signals will display the same dependence on the indicator particle concentration. The relative difference between the two signals is therefore only dependent on the distance between the indicator particles and the contact surface. Alternatively, independent distance measurements can be obtained using biosensors with single bead resolution.

Figure 5:
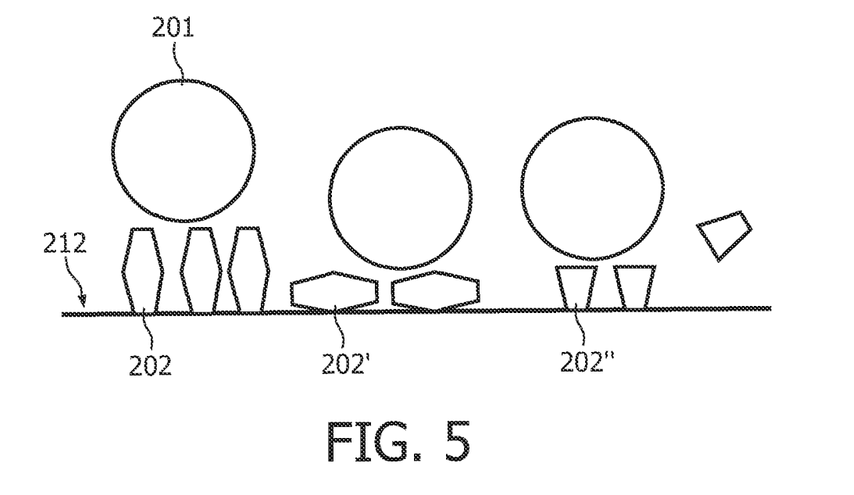
FIG. 5 illustrate the effect of conformational changes of target components.

The application of the proposed detection scheme is not only limited to detecting binding events of molecules with a size that is large enough to result in a height difference. In principle a (large enough) conformational change of a target molecule that is immobilized on the contact surface is sufficient to generate a signal change. As illustrated in FIG. 5, the distance an indicator particle 201 can assume from the contact surface 212 changes if a target molecule 202 undergoes a conformational change to a form 202' and/or if a part 202" of the molecule is split off. Conformational changes can be caused by e.g. a change in temperature, pH, ionic strength, binding of small molecules/ions or modification of the immobilized molecule by a chemical reaction/enzyme. The conformational change can be simply a change in shape of the molecule, but also a change in weight (e.g. dissociation of a protein from a complex, degradation of a protein by a protease, degradation of a nucleic acid by a nuclease). The ability to detect conformational changes therefore provides an important additional aspect of the present invention.

Figure 6A:
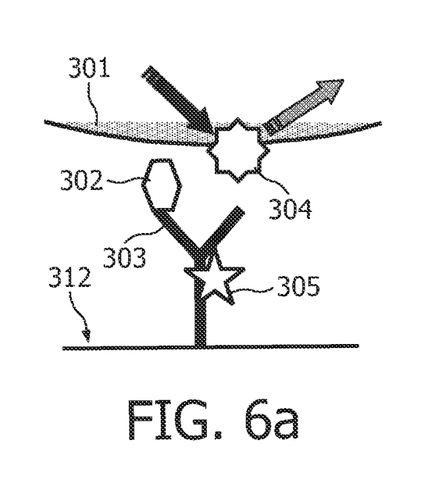
FIG. 6 illustrates the process of FRET at the contact surface.

FIG. 6 illustrates the application of fluorescence resonance energy transfer (FRET), which is another detection principle that has a sub-nanometer depth resolution. In FRET, the energy of an excited donor fluorophore 304 can be transferred to a nearby acceptor chromophore 305. In the shown example, an indicator particle 301 is labeled with a donor fluorophore 304 and the antibody 303 on the contact surface 312 with an acceptor fluorophore 305. The closer the indicator particle 301 can get to the surface, the more emission from the acceptor 305 will be observed. FIG. 6 a) illustrates the case that a target component 302 is bound to the antibody 303. The donor fluorophore 304 does not get close enough to the acceptor 305 and therefore emits after excitation (left arrow) light of a first wavelength (e.g. green).

Figure 6B:
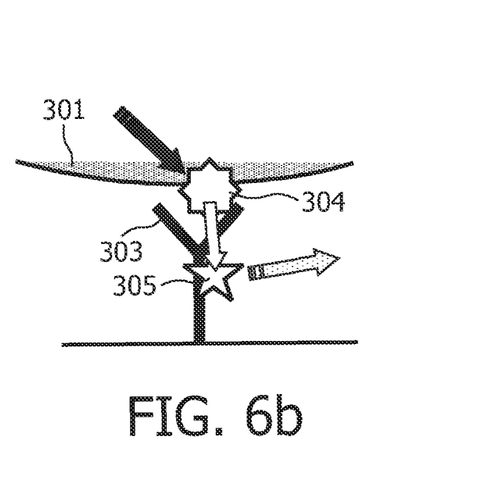

In FIG. 6 b), no target components are bound and the donor fluorophore 304 can get closer to the acceptor 305. Its excitation energy can therefore be transferred and emission of the acceptor 305 with a second wavelength (e.g. red) will be observed.

It should be noted that the roles of acceptor and donor can of course be exchanged in the above approach, i.e. the indicator particles may be labeled with an acceptor and the binding surface may carry a donor.

Figure 7A:
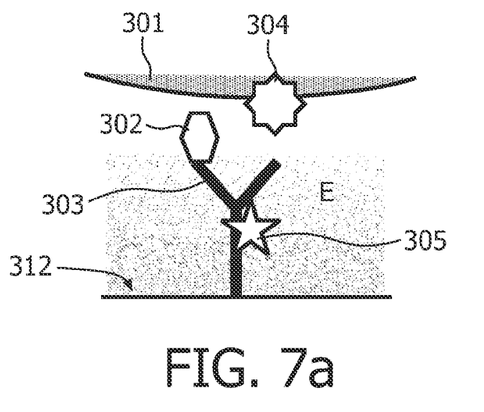
FIG. 7 illustrates the process of FRET during excitation with evanescent waves.
Figure 7B:
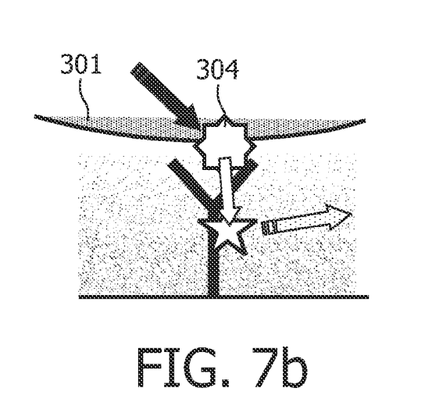

FIG. 7 illustrates a way to increase the distance dependence even further. This is achieved by exciting the fluorescent indicator particle 301 with the evanescent wave E of FTIR. If the donor fluorophore 304 is far from the contact surface 312 due to bound target components 302 (FIG. 1 a), it will be excited less due to the decreased intensity of the evanescent wave E. In addition, it can also transfer less energy to the acceptor 305, resulting in very little acceptor emission. However, if not target components are bound and the fluorophore 304 can come closer to the surface 312 (FIG. 7 b), it will be excited more and in addition more energy will be transferred to the acceptor 305, resulting in a large increase in acceptor emission.

Figure 8:
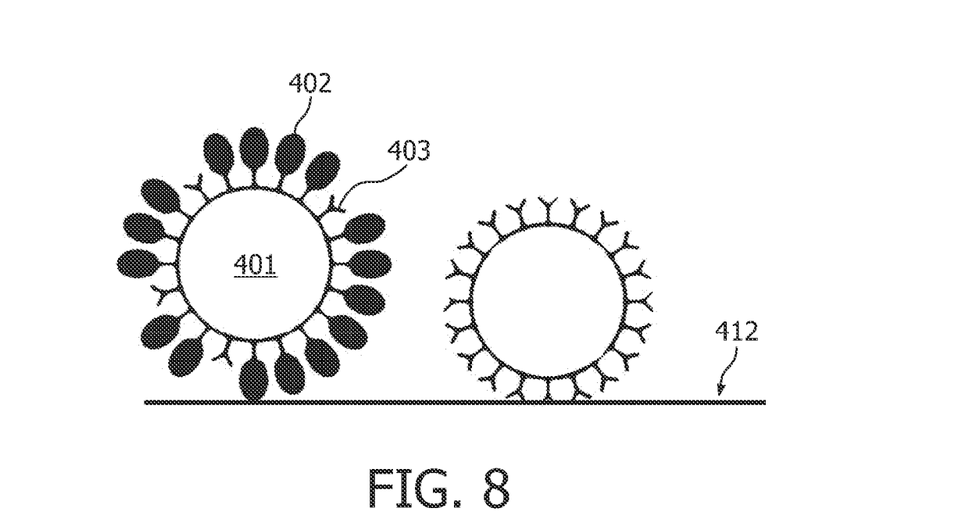
FIG. 8 illustrates the binding of target components to indicator particles.

FIG. 8 illustrates that the label-free assay can also be carried out in a "reversed format", using the indicator particle 401 (instead of the contact surface) as a solid state that is covered with specific binding sites 403 for target components 402. As above, the distance between the indicator particle 401 and the sensor surface 412 is dependent on the presence of the target components 401. The reversed format has the advantage that the binding reaction takes place in the bulk instead of on a single surface and therefore proceeds much faster. Furthermore, in this case the sensor surface does not need to be functionalized. Because it is difficult maintain protein (antibody) activity, especially on plastic surfaces, using simple plastic carriers (cartridges) without (printed) biomolecules greatly simplifies the cartridge manufacturing. Multiplexing using this format could be performed by e.g. using fluorescent beads of different colors and analyzing the height information for each color/wavelength independently.

The described methods of label-free detection have inter alia the following advantages:
  There is no need to attach proteins (e.g. antibodies) that can capture the target components to the magnetic particles (or the contact surface in the reversed format). The beads/surfaces are therefore easier to prepare and cheaper.
  Label-free detection avoids interferences of labeling with the biological function of a target molecule or with its binding to another molecule. Moreover, no knowledge of the molecule to be detected is required.
  In sandwich immunoassays, the target is sandwiched between two antibodies. This kind of assay can only be performed for targets with two epitopes that bind to the antibodies. However, there are also targets with only one epitope. For the label-free assay, only one antibody has to bind and therefore one epitope is sufficient.
  The label-free assay is not limited to immunoassays. In principle the binding of any molecule A to a molecule B that is immobilized on the surface can be detected, as long as the change in height is sufficient to generate a change in signal.
  Especially in screenings a large number of possible targets needs to be evaluated on their ability to bind to a specific molecule. It is very time consuming and expensive to label all targets that need to be investigated. Furthermore, if screening is done for yet unknown molecules, labeling can even be impossible. In addition, labeling of the target may lead to a decreased binding ability. Similarly, high multiplex arrays (e.g. DNA, RNA or protein arrays) consist of many spots of molecules immobilized on a surface that can each bind a different target. Also for these arrays it is very expensive if all the targets need to be labeled separately. All these problems are avoided with the proposed label-free detection.
  For most assay formats the first binding step (the capture) of a target component cannot be monitored in real-time, as a second binding step is required for the detection. The label-free assays described here can also be used to do real-time measurements: the detection takes place simultaneously and independent of the binding of target. Magnetic actuation of beads can also be used for mixing to speed up the reaction and for fluid excitation as a stringency (washing) process.

In summary, the invention relates to a system and a method for the detection of target components 102 in a sample with the help of indicator particles 101 distributed in said sample. The distance d between indicator particles 101 and a contact surface 112 is determined after the target components could bind to the contact surface and/or the indicator particles. Thus it is possible to detect how many target components 102 are bound without a need for a binding between indicator particles 101 and contact surface 112. Optionally the indicator particles 101 can be affected by a modulated (e.g. magnetic) force. The determination of the distance d between indicator particles 101 and contact surface 112 may for example be achieved by frustrated total internal reflection, measurement of magnetic fields, or FRET.

While the invention was described above with reference to particular embodiments, various modifications and extensions are possible, for example:

The sensor can be any suitable sensor to detect the presence of indicator particles on or near to a sensor surface, based on any property of the particles, e.g. it can detect via magnetic methods, optical methods (e.g. imaging, fluorescence, chemiluminescence, absorption, scattering, surface plasmon resonance, Raman, etc.), sonic detection (e.g. surface acoustic wave, bulk acoustic wave, cantilever, quartz crystal etc), electrical detection (e.g. conduction, impedance, amperometric, redox cycling), etc.

A magnetic sensor can be any suitable sensor based on the detection of the magnetic properties of the particle on or near to a sensor surface, e.g. a coil, magneto-resistive sensor, magneto-restrictive sensor, Hall sensor, planar Hall sensor, flux gate sensor, SQUID, magnetic resonance sensor, etc.

In addition to molecular assays, also larger moieties can be detected with sensor devices according to the invention, e.g. cells, viruses, or fractions of cells or viruses, tissue extract, etc.

The detection can occur with or without scanning of the sensor with respect to the sensor surface.

Measurement data can be derived as an end-point measurement, as well as by recording signals kinetically or intermittently.

The device and method are suited for sensor multiplexing (i.e. the parallel use of different sensors and sensor surfaces) and chamber multiplexing (i.e. the parallel use of different reaction chambers).

The device and method can be used as rapid, robust, and easy to use point-of-care biosensors for small sample volumes. The reaction chamber can be a disposable item to be used with a compact reader, containing the one or more field generating means and one or more detection means. Also, the device, methods and systems of the present invention can be used in automated high-throughput testing. In this case, the reaction chamber is e.g. a well-plate or cuvette, fitting into an automated instrument.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A sensor system for the detection of a parameter of interest that is related to target components in a sample, comprising:
    a) a sample chamber with a contact surface in which the sample can be provided, the contact surface being covered with acceptor chromophores or donor chromophores;
    b) a quantity of indicator particles that can be distributed in the sample and that do not directly or via target components bind to the contact surface;
    c) a sensor element configured to directly or implicitly measure a distance parameter indicative of a distribution of distances between indicator particles and the contact surface in a region adjacent to the contact surface, the sensor element including
    a light source arranged to emit an input light towards and onto the contact surface at an angle larger than a critical angle of total internal reflection (TIR) and a light detector arranged to detect one of (1) fluorescence of the indicator particles stimulated by an evanescent wave of the input light penetrating through the contact surface into the sample chamber and (2) frustrated total internal reflection (FTIR) of the input light caused by at least one of scattering and absorption by the indicator particles; and
    a microprocessor or FPGA configured to estimate the parameter of interest from the distance parameter.

2. The system as recited in claim 1, wherein the parameter of interest comprises at least one of the following values:
    the amount and/or concentration of target components;
    the absolute or relative amount of indicator particles to which target components are bound;
    the absolute or relative size of the contact surface to which tar components are bound;
    a chemical modification of the target components;
    a physical property of the sample that induces a change in the distance between the indicator particles and the contact surface, particularly the temperature, pH and/or ionic strength of the sample.

3. The system as recited in claim 1, wherein the indicator particles comprise magnetic beads, fluorescent particles, acceptor chromophores and/or donor chromophores.

4. The system as recited in claim 1, wherein a force is exerted on the indicator particles during the determination of their distance from the contact surface, particularly a modulated force.

5. The system as recited in claim 1, wherein the indicator particles are magnetized and that the distance between indicator particles and contact surface is determined by their effect on a magnetic field sensor.

6. The system as recited in claim 1, wherein the concentration of indicator particles in the sample is measured.

7. The system as recited in claim 1, wherein the sensor element is configured to measure at least two distance parameter measurements which depend in a different way on the concentration of the indicator particles and their distance from the contact surface.

8. The system as recited in claim 1, wherein the light detector is arranged to detect fluorescence of the indicator particles stimulated by an evanescent wave of the input light penetrating through the contact surface into the sample chamber.

9. The system as recited in claim 1, wherein the light detector is arranged to detect frustrated total internal reflection (FTIR) of the input light caused by at least one of scattering and absorption by the indicator particles.

10. The system as recited in claim 1, further including a magnetic field generator configured to controllably generate a magnetic field at the contact surface and in the adjacent space of the sample chamber.

11. A sensor device comprising:
a sample chamber with a contact surface;
a quantity of indicator particles disposed in the sample chamber and that do not directly or via target components bind to the contact surface; and
a sensor element configured to measure a distance parameter indicative of a distribution of distances between indicator particles and the contact surface in a region adjacent to the contact surface, the sensor element including:
a light source arranged to reflect an input light beam off the contact surface at an angle larger than a critical angle of total internal reflection (TIR), and
a light detector arranged to detect one of (1) fluorescence of the indicator particles stimulated by an evanescent wave of the input light reflected off the contact surface at said angle larger than the critical angle of TIR and (2) the input light reflected off the contact surface at said angle larger than the critical angle of TIR.

12. The sensor device of claim 11 wherein the light detector is arranged to detect fluorescence of the indicator particles stimulated by an evanescent wave of the input light reflected off the contact surface at said angle larger than the critical angle of TIR.

13. The sensor device of claim 11 wherein the light detector is arranged to detect the input light reflected off the contact surface at said angle larger than the critical angle of TIR.

14. The system as recited in claim 11, wherein the indicator particles comprise magnetic beads, fluorescent particles, acceptor chromophores and/or donor chromophores.

15. The system as recited in claim 11, wherein a modulated force is exerted on the indicator particles during the determination of their distance from the contact surface.

16. The system as recited in claim 11, wherein the indicator particles are magnetized and that the distance between indicator particles and contact surface is determined by their effect on a magnetic field sensor.

17. The system as recited in claim 11, wherein the light detector is arranged to detect fluorescence of the indicator particles stimulated by an evanescent wave of the input light penetrating through the contact surface into the sample chamber.

18. The system as recited in claim 11, wherein the light detector is arranged to detect frustrated total internal reflection (FTIR) of the input light caused by at least one of scattering and absorption by the indicator particles.

19. A sensor device comprising:
a sample chamber with a contact surface;
a quantity of indicator particles disposed in the sample chamber and that do not directly or via target components bind to the contact surface; and
a sensor element configured to measure a distance parameter indicative of a distribution of distances between indicator particles and the contact surface in a region adjacent to the contact surface, the sensor element including:
a light source arranged to reflect an input light beam off the contact surface at an angle larger than a critical angle of total internal reflection (TIR), and
a light detector arranged to detect one of (1) fluorescence of the indicator particles stimulated by an evanescent wave of the input light reflected off the contact surface at said angle larger than the critical angle of TIR and (2) the input light reflected off the contact surface at said angle larger than the critical angle of TIR;
wherein the contact surface is covered with acceptor chromophores or donor chromophores.

* * * * *